(12) United States Patent
Hojo et al.

(10) Patent No.: US 8,147,876 B2
(45) Date of Patent: Apr. 3, 2012

(54) MEDICAL AGENT FOR PREVENTING OR TREATING DISEASES RESULTING FROM ONE OF INFLAMMATION AND REMODELING, AND METHOD FOR PREVENTING OR TREATING THE DISEASES

(75) Inventors: Yukihiro Hojo, Kawachi-gun (JP); Kaneo Chiba, Higashimatsushima (JP); Yoshihiro Mano, Tokyo (JP)

(73) Assignees: National University Corporation Tokyo Medical and Dental University, Tokyo (JP); REO Laboratory, Co., Ltd., Higashimatsushima-Shi (JP)

( * ) Notice: Subject to any disclaimer, the term of this patent is extended or adjusted under 35 U.S.C. 154(b) by 984 days.

(21) Appl. No.: 12/071,747

(22) Filed: Feb. 26, 2008

(65) Prior Publication Data

US 2008/0220089 A1    Sep. 11, 2008

Related U.S. Application Data

(60) Provisional application No. 60/903,522, filed on Feb. 27, 2007.

(51) Int. Cl.
- *A61K 33/00* (2006.01)
- *A61K 9/00* (2006.01)
- *A61K 9/08* (2006.01)
- *A61P 9/00* (2006.01)
- *A61P 9/10* (2006.01)
- *A61P 9/12* (2006.01)

(52) U.S. Cl. ......... 424/613; 423/580.1; 423/581; 424/400; 514/824; 977/786; 977/908; 977/910; 977/915

(58) Field of Classification Search ............... None
See application file for complete search history.

(56) References Cited

U.S. PATENT DOCUMENTS

| | | | | |
|---|---|---|---|---|
| 6,649,145 B2 * | 11/2003 | McGrath et al. | ......... | 424/45 |
| 2006/0054205 A1 * | 3/2006 | Yabe et al. | ......... | 134/184 |
| 2007/0189972 A1 | 8/2007 | Chiba et al. | | |
| 2007/0286795 A1 * | 12/2007 | Chiba et al. | ......... | 423/580.1 |

FOREIGN PATENT DOCUMENTS

| | | |
|---|---|---|
| JP | 2005-245817 | 9/2005 |
| WO | WO 2005084786 A1 * | 9/2005 |

OTHER PUBLICATIONS

Cameron, Robert "Tiny Bubbles" Jun. 2005, American Chamber of Commerce in Japan Journal, pp. 35-36.*

* cited by examiner

*Primary Examiner* — Ernst Arnold
*Assistant Examiner* — Christopher R Lea
(74) *Attorney, Agent, or Firm* — Kratz, Quintos & Hanson, LLP

(57) ABSTRACT

An object of the present invention is to provide a medical agent that has an excellent effect on the diseases resulting from one of inflammation and remodeling and that can prevent or treat them in response to various mechanisms of onset and development of the diseases. Thus, the present invention relates to a medical agent for preventing or treating diseases resulting from one of inflammation and remodeling in blood vessel, including nanobubbles.

4 Claims, 13 Drawing Sheets control

OXNB

TNFα
cocultured with NR8383

TNFα: 20 ng/mL

OXNB+TNFα
cocultured with NR8383

TNFα: 20 ng/mL

TNFα 20 ng/mL

A II: 100nM, 5 min
EGF: 100 ng/mL, 5 min

Fig. 14
Normal rat
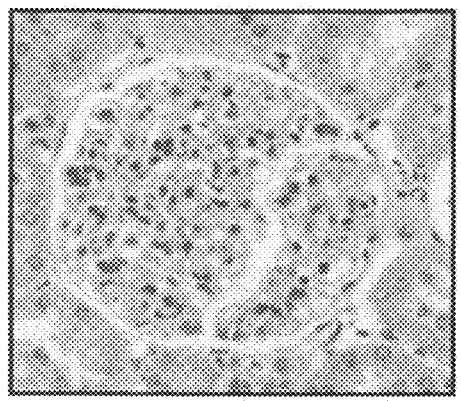
SHR, control
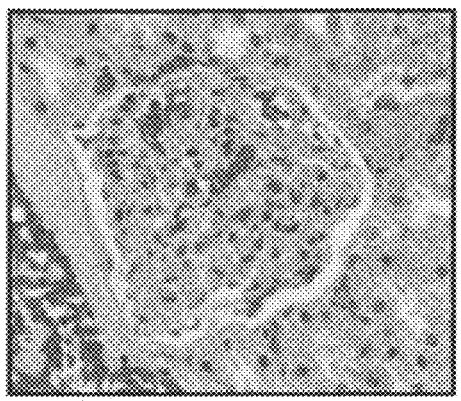
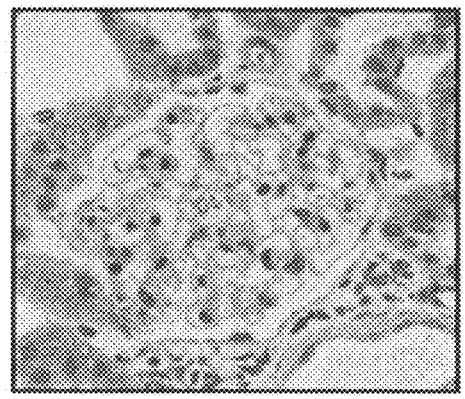
SHR, OXNB
Haematoxylin-Eosin staining

MEDICAL AGENT FOR PREVENTING OR TREATING DISEASES RESULTING FROM ONE OF INFLAMMATION AND REMODELING, AND METHOD FOR PREVENTING OR TREATING THE DISEASES

This application claims the benefit of U.S. Provisional Application No. 60/903,522, filed Feb. 27, 2007.

BACKGROUND OF THE INVENTION

1. Field of the Invention

The present invention relates to a medical agent for preventing or treating diseases resulting from inflammation or remodeling, particularly diseases such as arteriosclerosis, heart failure, cerebrovascular disorder, and hypertensive kidney disease; and to a method for preventing or treating the diseases.

2. Description of the Related Art

In recent years, with the aging of the population and Westernized eating habits, prevalence of high blood pressure, hyperlipemia, and diabetes has increased. As a result, arteriosclerotic diseases are increasing year by year. Arteriosclerotic diseases include diseases such as stroke, an ischemic heart disease, hypertensive nephropathy, ophthalmopathy, heart failure, aortic aneurysm, arteriosclerosis obliterans, hypertensive emergency, and cerebrovascular disorder. More than half of the elderly people aged 75 or more has some sort of disease and reduced quality of life (QOL). It is known that these diseases are caused by common pathologic conditions, arteriolar and aortic damages.

Chronic injury in endothelial cells triggers the onset of arteriosclerosis. Endothelial cells line the artery, forming a layer, and play an important role such as regulation of vascular permeability, production and/or secretion of antithrombotic substances, smooth muscle cell-growth inhibition, and production of vasoactive substances. In the injured vascular endothelium, these functions are impaired. In addition, on the surface of activated or injured endothelial cells, adhesion molecules such as intercellular adhesion molecule-1 (ICAM-1) and vascular cell adhesion molecule-1 (VCAM-1) are expressed. Monocyte recognizes adhesion molecules, adheres to the surface of endothelial cells, is recruited under the layer of endothelial cells, and then matures into a macrophage. The macrophage beneath endothelial cells is eventually converted into a foam cell, forming atherosclerotic plaque. Inflammatory cytokine is involved in the expression of adhesion molecules and migration of monocyte.

It is also known that in the pathologic condition such as high blood pressure that is involved in the development of arteriosclerosis, responding to various load applied on the blood vessel, the cytoarchitecture of blood vessel wall changes, causing remodeling of blood vessel. Remodeling of blood vessel refers to the change of the structure of vascular tissue as a result of the injury or abnormal proliferation of vascular tissue due to mechanical load or change of humoral factor. Originally, remodeling is a mechanism for responding to change in pathologic condition; it is known that remodeling has an adverse effect on blood vessel such as hardening of blood vessel wall and decrease of inner diameter during the process. It is known that in the remodeling of blood vessel, smooth muscle cells from medial layer in blood vessel, become hypertrophied. Growth factors such as angiotensin II and platelet derived growth factor (PDGF) are involved in this hypertrophy of smooth muscle cells.

As described above, the mechanism of onset and/or development of arteriosclerosis is complicated. Besides, many of the mechanisms are yet to be elucidated. There is a need for efficient methods for preventing and/or treating arteriosclerosis. Moreover, there is a need for efficient methods for preventing and/or treating diseases resulting from one of inflammation and remodeling including arteriosclerosis.

In recent years, attention has been paid to various bioactive effects of water that contains nanobubbles of oxygen in large amount (oxygen-nanobubble water) on living organisms. For example, oxygen-nanobubble water improves adaptability of fish and shellfish to environmental change, or restores a debilitated individual quickly. Nanobubbles are ultrafine bubbles with a nano-order diameter and are typically generated in the process where microbubbles (minute bubble with a diameter of 50 μm or less) shrink. Since nanobubbles are self-pressurized by the action of surface tension, they are completely dissolved rapidly. Thus, the lifetime was considered to be short in general. However, it is reported that in the case where nanobubbles are coated with shell by a surfactant, or in the case where they are subjected to electrostatic repulsion due to surface charging, even bubbles in nano-order can exist for a certain period. Especially, nanobubbles stabilized due to charging effect retain properties as bubble; thus various applications, such as direct action to organisms at cellular level, are expected (See, for example, Japanese Patent Application Laid-Open (JP-A) No. 2005-245817).

BRIEF SUMMARY OF THE INVENTION

An object of the present invention is to solve the conventional problems and to achieve the following objects. Specifically, an object of the present invention is to provide a medical agent that has an excellent preventive or therapeutic effect on the diseases resulting from one of inflammation and remodeling and that can prevent or treat them in response to various mechanisms of onset and development of the diseases.

As a result of dedicated investigations conducted by the present inventors to settle the above-mentioned problems, they have made the following findings. Specifically, they have found that nanobubble water which contains bubbles with a nano-order diameter can exhibit an excellent preventive or therapeutic effect on the diseases resulting from one of inflammation and remodeling.

As described above, it has been known that oxygen-nanobubble water which contains bubbles of oxygen with a nano-order diameter has various bioactive effects on living organisms. For example, it improves adaptability of fish and shellfish to environmental change, or restores a debilitated individual quickly. Thus, the oxygen-nanobubble water is attracting attention. In addition, recently a method for producing nanobubble water has been established that can maintain nanobubbles of oxygen or ozone stably for a long time (See, for example, JP-A No. 2005-245817).

Previously, however, it has not been known that the nanobubble water can exhibit an excellent preventive or therapeutic effect on the diseases resulting from one of inflammation and remodeling, which was newly found by the present inventors.

The present invention is based on the above-mentioned findings by the present inventors, and means for solving the above-mentioned problems are as follows. Specifically, <1> A medical agent for preventing or treating a disease resulting from one of inflammation and remodeling in blood vessel, including nanobubbles.
<2> The medical agent according to <1>, wherein the disease is at least one selected from arteriosclerosis, heart failure, cerebrovascular disorder, and hypertensive kidney disease.

<3> A histone H3 acetylation-inhibitor including nanobubbles.
<4> An ICAM-1 expression inhibitor including nanobubbles.
<5> A VCAM-1 expression inhibitor including nanobubbles.
<6> An inhibitor of adhesion of macrophage cells to vascular endothelial cells, including nanobubbles.
<7> An ERK activation inhibitor including nanobubbles.
<8> An EGF receptor transactivation-inhibitor including nanobubbles.
<9> A vascular smooth muscle cell hypertrophy-inhibitor including nanobubbles.
<10> An inhibitor for hypertensive glomerular injury, including nanobubbles.
<11> A method for preventing or treating a disease resulting from one of inflammation and remodeling in blood vessel, including administering the medical agent of <1> to a patient.

The present invention can solve the conventional problems and provide a medical agent that has an excellent effect on the diseases resulting from one of inflammation and remodeling and that can prevent or treat them. Nanobubble water affects various in vivo mechanisms associated with the diseases. Thus, the present invention can further provide a reagent and medicine for controlling these mechanisms.

BRIEF DESCRIPTION OF THE SEVERAL VIEWS OF THE DRAWINGS

FIG. 14 shows the results of hematoxylin-eosin staining of glomerular apparatus from 40-week-old rats in Example 3.

DETAILED DESCRIPTION OF THE INVENTION

Medical Agent for Prevention or Treatment

Figure 1:
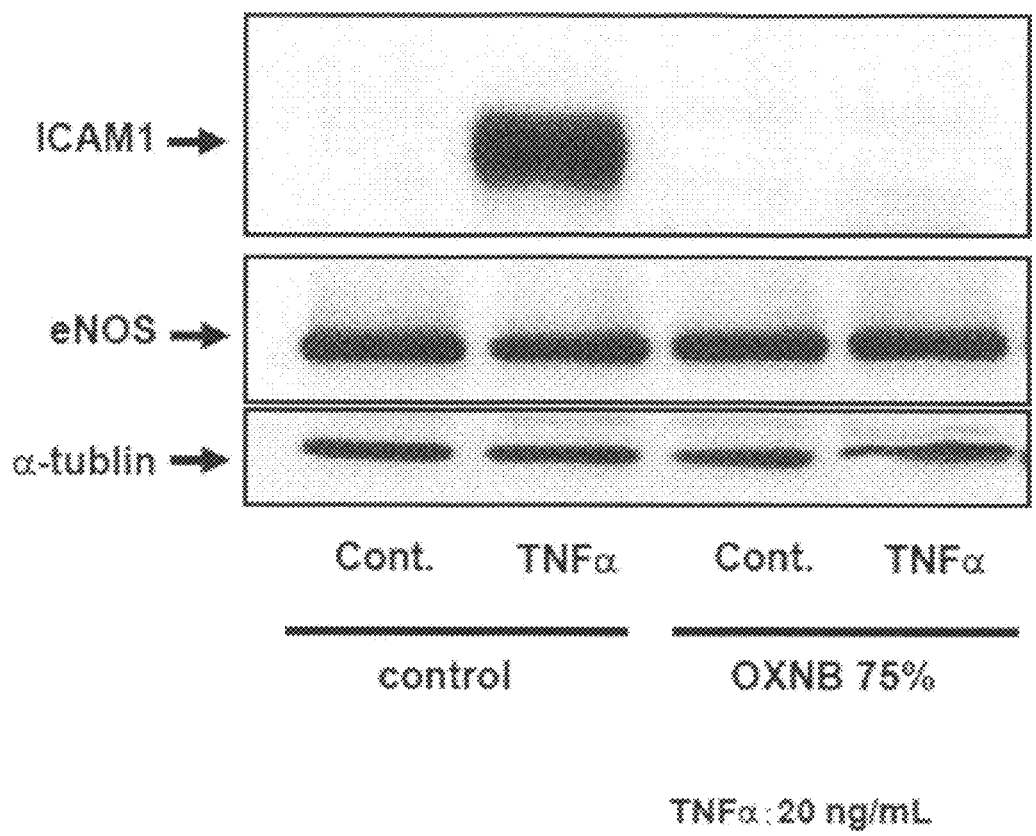
FIG. 1 shows results of Western blotting in Example 1.

The medical agent of the present invention comprises nanobubbles.

<Nanobubble>

In the present invention, the "nanobubble" refers to a bubble which has a nano-order diameter. The type of gas as the nanobubble is not particularly limited and can be appropriately selected according to the purpose. Examples thereof include oxygen, ozone, hydrogen, nitrogen, natural gas (e.g. methane), and the like. Among these, oxygen is preferable as the gas in that it has a better ability to treat diseases resulting from one of inflammation and remodeling in blood vessel. In the present invention, nanobubble composed of oxygen is particularly referred to as "oxygen nanobubble", and an aqueous solution that comprises the oxygen, part of which is in the form of the oxygen nanobubble, is particularly referred to as "oxygen nanobubble water".

The diameter of the nanobubble can be appropriately selected according to the purpose. The bubble diameter is preferably 200 nm or less, more preferably 100 nm or less and most preferably less than 10 nm. Nanobubbles with a diameter of 100 nm or less are advantageous in that there is less possibility for incorporation of electrolytes or foreign substances. It is considered that the smaller the diameter is, the more stable in long-term storage the nanobubbles are, and the less impurity the nanobubbles contain. Nanobubbles with a diameter less than 10 nm are further advantageous in that incorporation of many foreign substances including viruses can be prevented.

The bubble diameter of the nanobubble can be adjusted to a desired size using, for example, a reverse osmosis membrane (for ozone nanobubble, use of reverse osmosis membrane is not appropriate). The bubble diameter of the nanobubble can be measured with, for example, a dynamic light scattering equipment.

As long as at least part of bubble contained in the medical agent exists as the nanobubble, the medical agent may comprise, in addition to the nanobubble, bubble with a larger diameter (for example, bubble which has a micro-order diameter (more than 1 μm, and 1 mm or less)). The concentration of the nanobubble in the tissue repair and/or regeneration solution is particularly preferably saturated one. It is important that nanobubble be dissolved in the solution sufficiently.

The solution that makes up the medical agent is preferably an aqueous solution, but other liquids can be appropriately selected according to the purpose.

—Other Component—

The nanobubble water may comprise other components than the nanobubbles as necessary. The other component is not particularly limited and can be appropriately selected according to the purpose, including, for example, iron, manganese, and salts.

The salt concentration, pH, and hardness of the nanobubble water are not particularly limited and can be appropriately selected according to the purpose. For example, each of them can be adjusted to a desired degree during the production process of nanobubble water described below or after the production of nanobubble water.

—Production—

The nanobubble water can be produced by any method without limitation and the method can be appropriately selected depending on the application. For example, the nanobubble water can be produced by the production method disclosed in JP-A Nos. 2005-245817, 2005-246294, etc. The production method disclosed in the gazette is preferable since it can produce nanobubble water in which nanobubbles exist stably and do not disappear from the aqueous solution over a long period of several months or more.

In the production process of the nanobubble water, iron, manganese, and/or salts can be preferably added.

The salt concentration of the aqueous solution used in the production process of the nanobubble water is preferably 0.2% by mass to 3.0% by mass, and more preferably 0.8% by mass to 1.2% by mass. When the salt concentration is within the range of from 0.8% by mass to 1.2% by mass, nanobubbles (core of gas) can be produced easily; thus it is advantageous in that production efficiency of the nanobubble water is excellent. The salt concentration can be measured using, for example, a known instrument for measuring salt concentration.

It is considered that the pH and hardness of the aqueous solution used in the production process of the nanobubble water does not affect the production efficiency of nanobubbles as greatly as does the salt concentration. Typically, the pH is preferably 7 to 8, and the hardness is preferably 20 to 30. The pH and hardness can be measured using, for example, a known instrument for measuring pH and a known instrument for measuring hardness, respectively.

More specifically, microbubbles of 50 μm or less are produced using hard water (groundwater) with a salt concentration of 1.0% by mass as a raw material. Then, by rapidly collapsing or crushing the microbubbles, nanobubble water can be produced. Further, nanobubble water with a salt concentration of 0% by mass can be prepared by passing the resulting nanobubble water through a reverse osmosis membrane of 10 angstrom twice (oxygen-nanobubble water with a salt concentration of 0% by mass is "Naga no shizuku" (drips of Naga) (manufactured by NAGA Co., Ltd.), which is drinking water approved by the Ministry of Health, Labour and Welfare.). Meanwhile, nanobubble water with a salt concentration of 1.0% by mass is nanobubble water that is not passed through a reverse osmosis membrane of 10 angstrom. Varying the mixing ratio of both of the nanobubble waters can provide nanobubble waters with a salt concentration of from 0% by mass to 1.0% by mass. As mentioned above, in the case of ozone nanobubble, use of reverse osmosis membrane is not preferable because when ozone nanobubble water is passed through a reverse osmosis membrane, device may melt and get damaged.

The nanobubble water, prepared as described above, may be used itself as the medical agent, or may be used as the medical agent by combining with other components. For example, it is expected that the ability to prevent or treat diseases resulting from one of inflammation and remodeling in blood vessel can be further improved by adding to the nanobubble water an existing medical agent, etc. that can be used for the purpose of prevention or treatment of diseases resulting from one of inflammation and remodeling in blood vessel, or by using the nanobubble water for preparing an existing medical agent, etc. that can be used for the purpose of prevention or treatment of diseases resulting from one of inflammation and remodeling in blood vessel. Thus, such medical agents that utilize the nanobubble water in part are also included within the scope of the medical agent of the present invention.

<Aspect of Medical Agent>

Since the medical agent has excellent capability of prevention or treatment of diseases resulting from one of inflammation and remodeling in blood vessel, it is suitable for animals, tissues, and the prevention or treatment of diseases.

—Target Animal—

The animal, to which the medical agent is applied, is not particularly limited, including those from mammals, birds, reptiles, amphibian, and the like. Among these, mammals are preferable. The mammal is not particularly limited, and examples thereof include human, monkey, cattle, horses, pigs, mice, rats, and the like. Among these, human is preferable.

—Target Tissue—

The tissue, to which the medical agent is applied, is not particularly limited and can be appropriately selected according to the purpose; examples thereof include epithelial tissue, connective tissue, muscular tissue, nerve tissue, and the like. The word "tissue" also includes "cells" and "organs" below. The "cell" is not particularly limited and can be appropriately selected according to the purpose; examples thereof include epidermal cells, pancreatic parenchymal cells, pancreatic ductal cells, hepatic cells, blood cells, cardiac muscle cells, skeletal muscle cells, osteoblasts, skeletal myoblasts, nerve cells, endothelial cells, pigment cells, smooth muscle cells, fat cells, bone cells, cartilage cells, and the like. The "organ" is not particularly limited and can be appropriately selected according to the purpose; examples thereof include skin, blood vessel, cornea, kidney, heart, liver, umbilical cord, intestine, nerve, lung, placenta, pancreas, brain, peripheral extremities, retina, and the like.

The organism from which the tissue is derived is not particularly limited and can be appropriately selected according to the purpose. Mammals are preferable, and human is more preferable.

The tissue may be those present inside of the body, or may be those present outside of the body (for example, cultured tissue).

—Target Diseases—

The disease, to which the medical agent is applied, is not particularly limited as long as the disease is diseases resulting from one of inflammation and remodeling in blood vessel that can occur in the target tissue which the target animal has, and the disease can be appropriately selected according to the purpose. Specific examples of the disease resulting from inflammation in blood vessel include acute coronary syndrome resulting from rupture of coronary atheroma (acute myocardial infarction and unstable angina), aortitis syndrome, Buerger's disease, Kawasaki disease, and the like. Specific examples of the disease resulting from remodeling in blood vessel include hypertension, arteriosclerosis, diabetic macro- and microangiopathy, restenosis after angioplasty, arteriovenous shunt stenosis, graft angiostenosis, aortic aneurysm, arteriovenous fistula, arteriosclerosis after heart or kidney transplantation, nephrosclerosis, pulmonary hypertension, and the like. Examples of the disease, with which arteriosclerosis is deeply associated and which is caused or developed by inflammation or remodeling, include stroke, an ischemic heart disease, hypertensive nephropathy, ophthalmopathy, heart failure, aneurysm, arteriosclerosis obliterans, hypertensive emergency, cerebrovascular disorder, and the like.

—Usage—

The medical agent can be used in any manner without limitation as long as the effect of the present invention is achieved, and the manner can be appropriately selected according to the purpose. For example, the medical agent can be used by contacting with the tissue in blood vessel where inflammation and/or remodeling is/are caused by any method.

The medical agent can be stored in any way without limitation and the way can be appropriately selected according to the purpose. When ozone-nanobubble is used, it is preferable that the medical agent be shielded from ultraviolet light and refrigerated under dark.

<Other Use>

The present inventors revealed that nanobubble water is involved in various mechanisms related to the diseases resulting from one of inflammation and remodeling in blood vessel.

Thus, nanobubble water not only can be used as a medical agent for the prevention or treatment of diseases resulting from one of inflammation and remodeling in blood vessel, but also can be put to various uses shown below.

—Histone H3 Acetylation-Inhibitor—

The histone H3 acetylation-inhibitor of the present invention comprises nanobubbles. Of course, if necessary, other components can be appropriately selected. The histone H3 acetylation-inhibitor includes both an inhibitor used for reagent and an inhibitor used for prevention and/or treatment of diseases.

The histone H3 acetylation-inhibitor has an effect to inhibit acetylation of histone H3, particularly has an effect to inhibit acetylation of histone H3, which is induced by tumor necrosis factor α (TNF α) stimulation. Such effect allows us to utilize the histone H3 acetylation-inhibitor for the studies of acetylation mechanism of histone H3, chromatin structure controlled by the acetylation of histone H3, transcriptional mechanism of a specific gene, which is controlled by the chromatin structure, relative increase in histone acetylation due to reduced histone deacetylation, and diseases exacerbated by the acetylation of histone H3; and for the prevention or treatment of diseases exacerbated by the acetylation of histone H3. The disease exacerbated by the acetylation of histone H3 also includes the target diseases listed in the section of (medical agent for prevention or treatment).

The histone H3 acetylation-inhibitor may be used in any manner without limitation as long as the effect of the present invention is achieved, and the manner can be appropriately selected according to the purpose. For example, the histone H3 acetylation-inhibitor can be used by contacting with the tissue in blood vessel where inflammation and/or remodeling is/are caused by any method.

—Intercellular Adhesion Molecule-1 (ICAM-1) Expression Inhibitor—

The ICAM-1 expression inhibitor of the present invention comprises nanobubbles. Of course, if necessary, other components can be appropriately selected. The ICAM-1 expression inhibitor includes both an inhibitor used for reagent and an inhibitor used for prevention and/or treatment of diseases.

The ICAM-1 expression inhibitor has an effect to inhibit expression of ICAM-1, particularly has an effect to inhibit expression of ICAM-1, which is induced by interleukin-1β (IL-1β) stimulation and TNF α stimulation. Such effect allows us to utilize the ICAM-1 expression inhibitor for the studies of expression mechanism of ICAM-1, factors adhering to ICAM-1, abnormality in ICAM-1 function, and diseases exacerbated by the expression of ICAM-1; and for the prevention or treatment of diseases exacerbated by the expression of ICAM-1. The disease exacerbated by the expression of ICAM-1 also includes the target diseases listed in the section of (medical agent for prevention or treatment).

The ICAM-1 expression inhibitor can be used in any manner without limitation as long as the effect of the present invention is achieved, and the manner can be appropriately selected according to the purpose. For example, the ICAM-1 expression inhibitor can be used by contacting with the tissue in blood vessel where inflammation and/or remodeling is/are caused by any method.

—Vascular Cell Adhesion Molecule-1 (VCAM-1) Expression Inhibitor—

The VCAM-1 expression inhibitor of the present invention comprises nanobubbles. Of course, if necessary, other components can be appropriately selected. The VCAM-1 expression inhibitor includes both an inhibitor used for reagent and an inhibitor used for prevention and/or treatment of diseases.

The VCAM-1 expression inhibitor has an effect to inhibit expression of VCAM-1, particularly has an effect to inhibit expression of VCAM-1, which is induced by IL-1β stimulation and TNF α stimulation. Such effect allows us to utilize the VCAM-1 expression inhibitor for the studies of expression mechanism of VCAM-1, factors adhering to VCAM-1, abnormality in VCAM-1 function, and diseases exacerbated by the expression of VCAM-1; and for the prevention or treatment of diseases exacerbated by the expression of VCAM-1. The disease exacerbated by the expression of VCAM-1 also includes the target diseases listed in the section of (medical agent for prevention or treatment).

The VCAM-1 expression inhibitor can be used in any manner without limitation as long as the effect of the present invention is achieved, and the manner can be appropriately selected according to the purpose. For example, the VCAM-1 expression inhibitor can be used by contacting with the tissue in blood vessel where inflammation and/or remodeling is/are caused by any method.

—Inhibitor of Adhesion of Macrophage Cells to Vascular Endothelial Cells—

The inhibitor of adhesion of macrophage cells to vascular endothelial cells comprises nanobubbles. Of course, if necessary, other components can be appropriately selected. The inhibitor of adhesion of macrophage cells to vascular endothelial cells includes both an inhibitor used for reagent and an inhibitor used for prevention and/or treatment of diseases.

The inhibitor of adhesion of macrophage cells to vascular endothelial cells has an effect to inhibit adhesion of macrophage cells to vascular endothelial cells, particularly has an effect to inhibit adhesion through ICAM-1 and VCAM-1 expressed on the surface of vascular endothelial cell. Such effect allows us to utilize the inhibitor of adhesion of macrophage cells to vascular endothelial cells for the studies of adhesion mechanism of macrophage cells to vascular endothelial cells, factors adhering to macrophage cell, diseases caused by abnormal macrophage migration, and diseases exacerbated by the adhesion of macrophage cells to vascular endothelial cells; and for the prevention or treatment of diseases caused by abnormal macrophage migration and diseases exacerbated by the adhesion of macrophage cells to vascular endothelial cells. The disease caused by abnormal macrophage migration and disease exacerbated by the adhesion of macrophage cells to vascular endothelial cells also include the target diseases listed in the section of (medical agent for prevention or treatment).

The inhibitor of adhesion of macrophage cells to vascular endothelial cells can be used in any manner without limitation as long as the effect of the present invention is achieved, and the manner can be appropriately selected according to the purpose. For example, the inhibitor of adhesion of macrophage cells to vascular endothelial cells can be used by contacting with the tissue in blood vessel where inflammation and/or remodeling is/are caused by any method.

—Extracellular Signal Regulated Kinase (ERK) Activation Inhibitor—

The ERK activation inhibitor of the present invention comprises nanobubbles. Of course, if necessary, other components can be appropriately selected. The ERK activation inhibitor includes both an inhibitor used for reagent and an inhibitor used for prevention and/or treatment of diseases.

The ERK activation inhibitor has an effect to inhibit activation of ERK, particularly has an effect to inhibit activation of ERK due to angiotensin II (A II) stimulation, or activation of ERK via tyrosine phosphorylation of EGF receptor. Such effect allows us to utilize the ERK activation inhibitor for the studies of mechanism of ERK activation, factors controlled by ERK activation, abnormal cellular proliferation and/or differentiation through ERK activation, and diseases exacerbated by the ERK activation; and for the prevention or treatment of diseases exacerbated by the ERK activation. The disease exacerbated by the ERK activation also includes the target diseases listed in the section of (medical agent for prevention or treatment).

The ERK activation inhibitor can be used in any manner without limitation as long as the effect of the present invention is achieved, and the manner can be appropriately selected according to the purpose. For example, the ERK activation inhibitor can be used by contacting with the tissue in blood vessel where inflammation and/or remodeling is/are caused by any method.

—Epidermal Growth Factor (EGF) Receptor Transactivation-Inhibitor—

The EGF receptor transactivation-inhibitor of the present invention comprises nanobubbles. Of course, if necessary, other components can be appropriately selected. The EGF receptor transactivation-inhibitor includes both inhibitors used for reagent and inhibitors used for prevention and/or treatment of diseases.

The "EGF receptor transactivation" means that EGF receptor is not activated directly by its ligand, EGF, but is activated secondarily by the activation of G protein-coupled receptor such as angiotensin II. It is considered that transactivation has an important role on the mechanism of hypertrophy by angiotensin II.

The EGF receptor transactivation-inhibitor has an effect to inhibit transactivation of EGF receptor, particularly has an effect to inhibit transactivation of EGF receptor due to angiotensin II stimulation. Such effect allows us to utilize the EGF receptor transactivation-inhibitor for the studies of mechanism of EGF receptor transactivation, factors controlled by EGF receptor transactivation, elucidation of mechanism of EGF receptor transactivation, and diseases exacerbated by the EGF receptor transactivation; and for the prevention or treatment of diseases exacerbated by the EGF receptor transactivation. The disease exacerbated by the EGF receptor transactivation also includes the target diseases listed in the section of (medical agent for prevention or treatment).

The EGF receptor transactivation-inhibitor can be used in any manner without limitation as long as the effect of the present invention is achieved, and the manner can be appropriately selected according to the purpose. For example, the EGF receptor transactivation-inhibitor can be used by contacting with the tissue in blood vessel where inflammation and/or remodeling is/are caused by any method.

—Vascular Smooth Muscle Cell Hypertrophy-Inhibitor—

The vascular smooth muscle cell hypertrophy-inhibitor of the present invention comprises nanobubbles. Of course, if necessary, other components can be appropriately selected. The vascular smooth muscle cell hypertrophy-inhibitor includes both inhibitors used for reagent and inhibitors used for prevention and/or treatment of diseases.

The vascular smooth muscle cell hypertrophy-inhibitor has an effect to inhibit hypertrophy of vascular smooth muscle cell, particularly has an effect to inhibit hypertrophy of vascular smooth muscle cell due to angiotensin II stimulation and platelet derived growth factor (PDGF) stimulation. Such effect allows us to utilize the vascular smooth muscle cell hypertrophy-inhibitor for the studies of mechanism of vascular smooth muscle cell hypertrophy, factors controlled by vascular smooth muscle cell hypertrophy, elucidation of mechanism of vascular smooth muscle hypertrophy, and diseases exacerbated by the vascular smooth muscle cell hypertrophy; and for the prevention or treatment of diseases exacerbated by the vascular smooth muscle cell hypertrophy. The disease exacerbated by the vascular smooth muscle cell hypertrophy also includes the target diseases listed in the section of (medical agent for prevention or treatment).

The vascular smooth muscle cell hypertrophy-inhibitor can be used in any manner without limitation as long as the effect of the present invention is achieved, and the manner can be appropriately selected according to the purpose. For example, the vascular smooth muscle cell hypertrophy-inhibitor can be used by contacting with the tissue in blood vessel where inflammation and/or remodeling is/are caused by any method.

—Inhibitor for Hypertensive Glomerular Injury—

The inhibitor for hypertensive glomerular injury of the present invention comprises nanobubbles. Of course, if necessary, other components can be appropriately selected. The inhibitor for hypertensive glomerular injury includes both inhibitors used for reagent and inhibitors used for prevention and/or treatment of diseases.

The inhibitor for hypertensive glomerular injury has an effect to prevent or treat hypertensive glomerular injury, particularly has an effect on hypertensive glomerular injury exacerbated by the intake of salts. Such effect allows us to utilize the inhibitor for hypertensive glomerular injury for the studies of mechanism of hypertensive glomerular injury, factors controlled by hypertensive glomerular injury, and diseases exacerbated by the hypertensive glomerular injury; and for the prevention or treatment of diseases exacerbated by the hypertensive glomerular injury. The disease exacerbated by the hypertensive glomerular injury also includes the target diseases listed in the section of (medical agent for prevention or treatment).

The inhibitor for hypertensive glomerular injury can be used in any manner without limitation as long as the effect of the present invention is achieved, and the manner can be appropriately selected according to the purpose. For example, the inhibitor for hypertensive glomerular injury can be used by contacting with the tissue in blood vessel where inflammation and/or remodeling is/are caused by any method.

Due to the effect of nanobubble, the medical agent for prevention or treatment of the present invention can be suitably used for prevention or treatment of diseases resulting from one of inflammation and remodeling in blood vessel. In addition, the effect of nanobubble has an influence on various in vivo mechanisms associated with the diseases. For example, the medical agent can be used as a histone H3 acetylation-inhibitor, ICAM-1 expression inhibitor, VCAM-1 expression inhibitor, inhibitor of adhesion of macrophage cells to vascular endothelial cells, ERK activation inhibitor, EGF receptor transactivation-inhibitor, vascular smooth muscle cell hypertrophy-inhibitor, and inhibitor for hypertensive glomerular injury.

EXAMPLES

Hereinafter, Examples of the present invention will be described, which however shall not be construed as limiting the present invention thereto.

In Examples, OXNB means oxygen nanobubble, and OZNB means ozone nanobubble. Both are available from REO Institute.

Example 1

Objective:
To investigate the effect of nano-bubbles on inflammatory responses in the cultured endothelial cells induced by cytokines.

Methods:
(1) Medium preparation: Although accurate assay for OXNB density is not established, the activity of OXNB is increased with increasing the concentration of NaCl in the solution. REO Institute provided us OXNB solution including 1.0% by mass of NaCl. We prepared NaCl-free MCDB medium powder and dissolved the powder by using OXNB solution as vehicle. Because ordinary MCDB media contains 0.64% by mass of NaCl, we diluted the nano-bubble solution by distilled water to make OXNB with 0.64% by mass of NaCl. Then we dissolved the sodium free-MCDB medium powder with 0.64% by mass of NaCl OXNB solution to adjust NaCl concentration to ordinary MCDB media and defined the media 100%-OXNB MCDB. To examine the dose-response relationship between inflammatory response and concentration of OXNB, we diluted 100%-OXNB MCDB by ordinary MCDB media. The "50%-OXNB" and "75%-OXNB" described below mean those prepared by diluting 100%-OXNB MCDB by ordinary MCDB media (based on mass).

(2) Cell culture: Rat aortic endothelial cells (RAOECs, passage 7 to 10) were incubated in the MCDB culture media (containing fetal bovine serum, endothelial cell growth factor and antibiotics) with or without OXNB for 24 hours and were stimulated with inflammatory cytokines (10 ng/mL of IL-1β or 20 ng/mL of TNFα). Expression of intercellular adhesion molecule-1 (ICAM-1), vascular cell adhesion molecule-1 (VCAM-1), endothelial NO synthase (eNOS) and α-tubulin was examined by Western blotting.

(3) Analysis of mRNA expression: Northern blot analysis was performed to examine mRNA expression of ICAM-1 and VCAM-1 induced by inflammatory cytokines 6 hours after the stimulation.

(4) Functional analysis: RAOECs were incubated either with or without OXNB. Rat alveolar macrophage cells (NR8383) were stimulated with 0.1 μM of lipopolysaccharide (LPS). Then RAOECs and NR8383 were co-cultured for 1 hour and adhesion of NR8383 to RAOECs was evaluated.

(5) Signal transduction experiments: RAOECs were incubated in the culture media with or without OXNB for 24 hours and were stimulated with 20 ng/mL of TNFα. Intracellular signal transduction was evaluated by Western blot analysis. Activation of NFkB was measured by NFKB p50/65 transcription factor assay kit (Chemicon International Inc.) (DiDonato J A, Mercurio F, Karin M.: Phosphorylation of IKBa precedes but is not sufficient for its dissociation from NF-kB. Mol. Cell. Biol. 1995; 15: 1302-1311; Huang T, Miyamoto S.: Postrepression activation of NF-kB requires the amino-terminal nuclear export signal of IKBa. Mol. Cell. Biol. 2001; 21: 4737-1311).

(6) Histone acetyltransferase (HAT) activity: HAT activity was measured by commercially available kit (Upstate Biotechnologies Inc.) (Dignam J D, Lebovits R M, Roeder R G.: Accurate transcription initiation by RNA polymerase II in a soluble extract from isolated mammalian nuclei. Nucleic Acid Res. 1983; 11: 1475-1489; Nakatani F, Tanaka K, Sakimura R et al.: Identification of p21WAF/CIP1 as a direct target of EWS-Fli1 oncogenic fusion protein. J Biol Chem. 2003; 278: 15105-15115).

Figure 2:
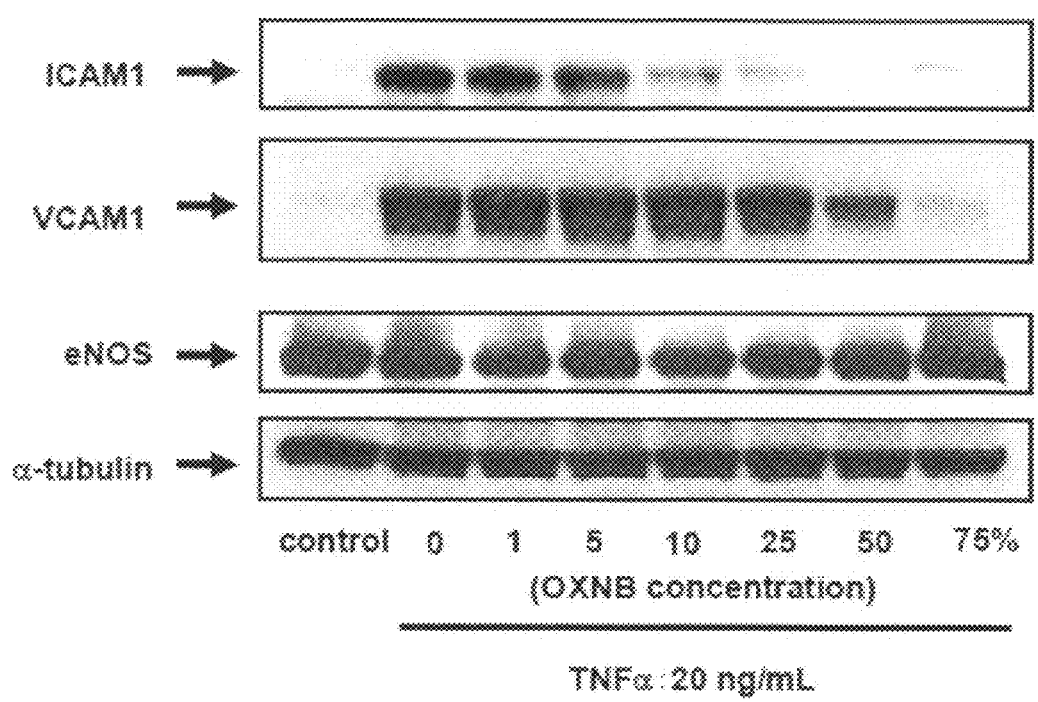
FIG. 2 shows results of Western blotting in Example 1.
Figure 3:
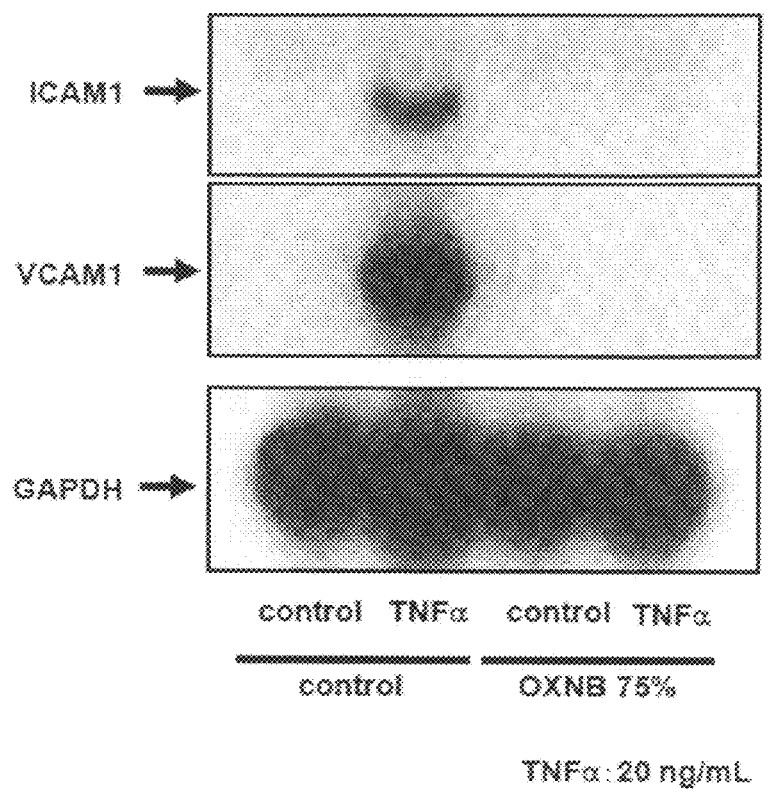
FIG. 3 shows results of Northern blot analysis in Example 1.
Figure 4A:
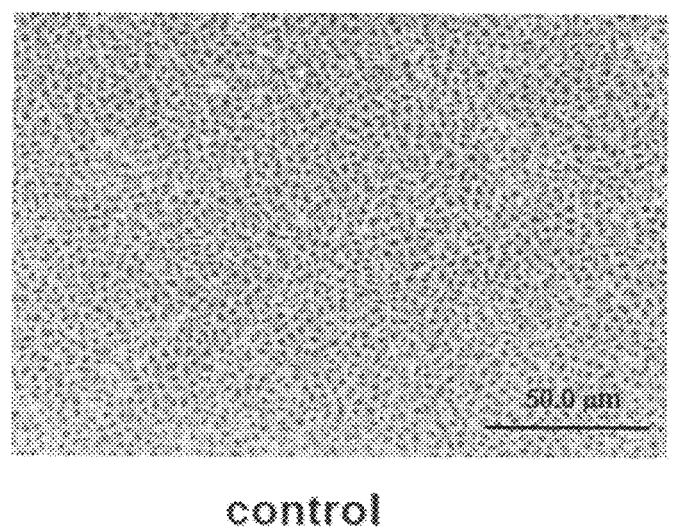
FIG. 4A is an optical microscope image showing a result of functional analysis in Example 1.
Figure 4B:
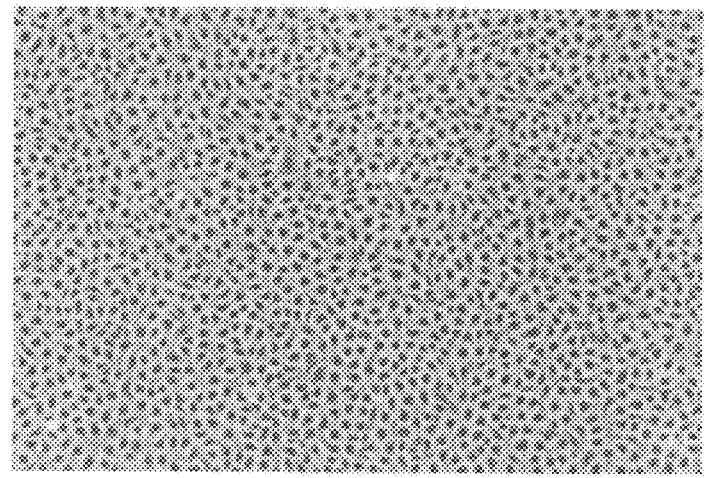
FIG. 4B is an optical microscope image showing a result of functional analysis in Example 1.
Figure 4C:
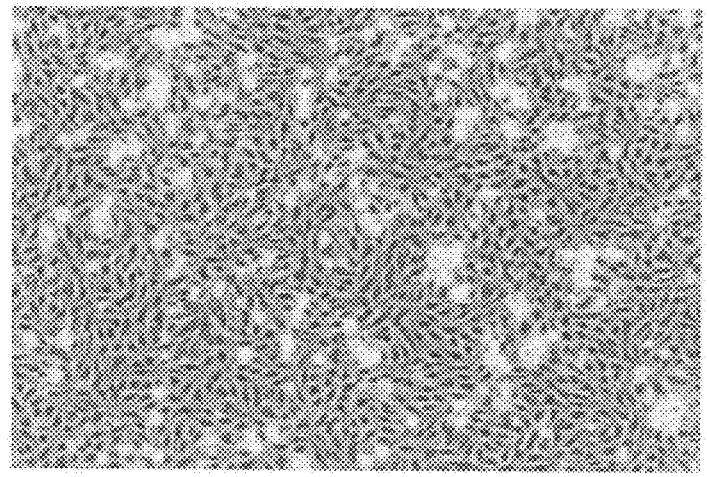
FIG. 4C is an optical microscope image showing a result of functional analysis in Example 1.
Figure 4D:
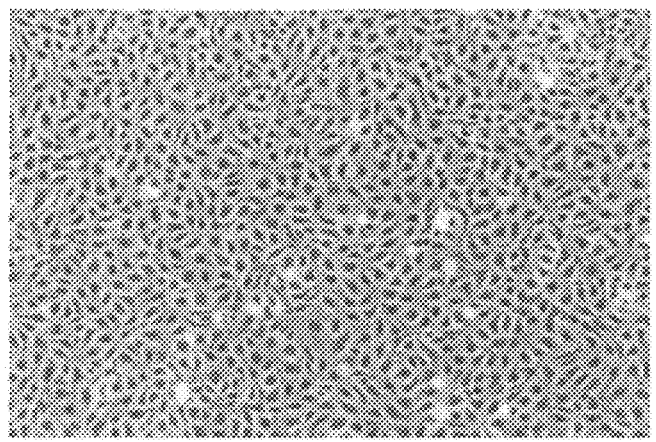
FIG. 4D is an optical microscope image showing a result of functional analysis in Example 1.
Figure 5:
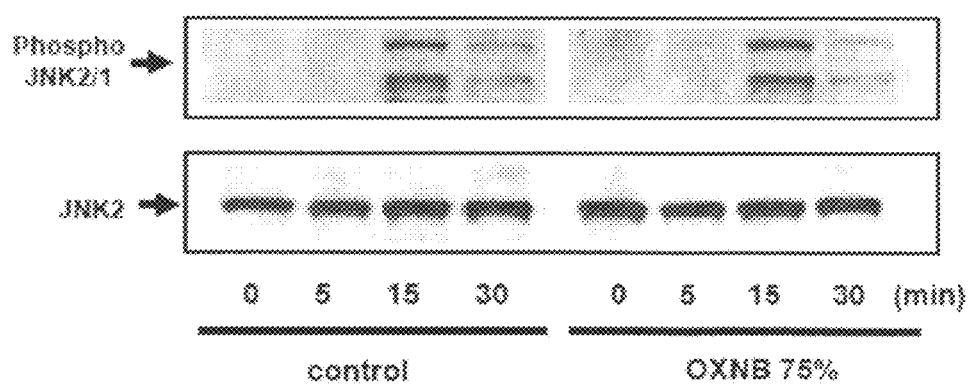
FIG. 5 shows results of signal transduction experiments in Example 1.
Figure 6A:
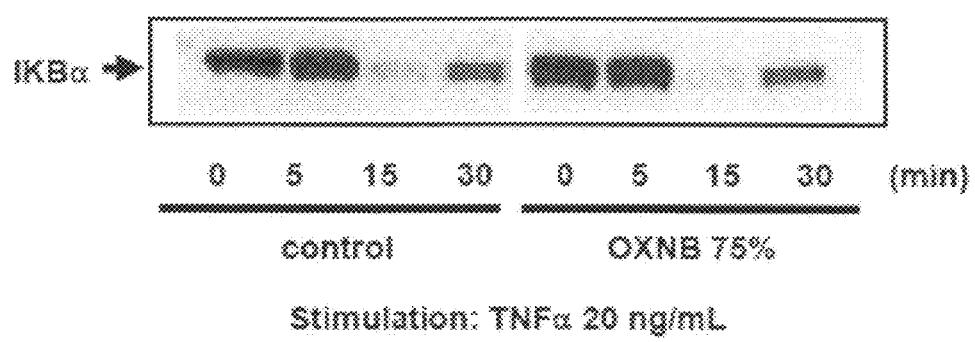
FIG. 6A shows results of signal transduction experiments in Example 1.
Figure 6B:
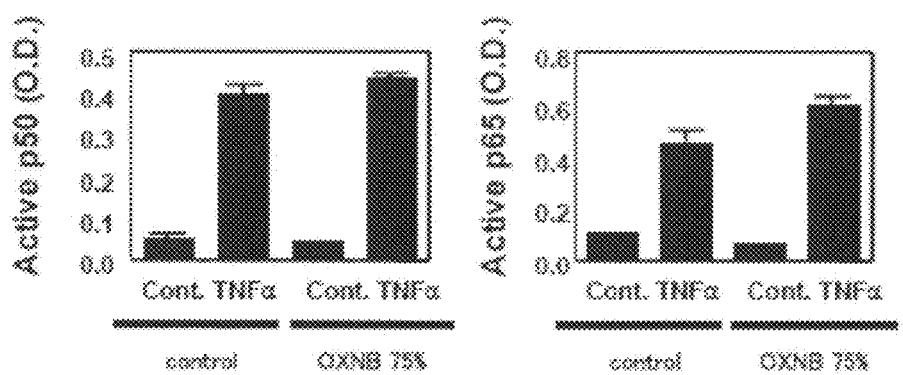
FIG. 6B shows results of signal transduction experiments in Example 1.
Figure 7:
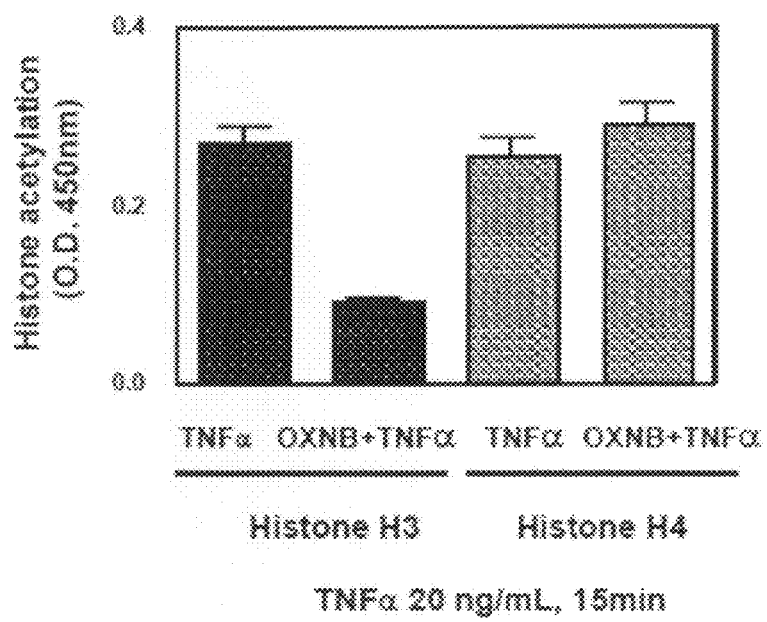
FIG. 7 shows results of the evaluation of histone acetyltransferase (HAT) activity in Example 1.

Results:
IL-1β and TNFα induced ICAM-1 and VCAM-1 expression in RAOECs with a peak at 24 hours after stimulation. Incubation of RAOECs with culture media containing OXNB inhibited induction of ICAM-1 by TNFα (FIG. 1). ICAM-1 expression was perfectly abolished over 50%-OXNB media and VCAM-1 expression was perfectly abolished over 75%-OXNB media (FIG. 2). In contrast, expression of eNOS or α-tublin was not changed. Northern blot analysis revealed that OXNB inhibited induction of mRNA expression of ICAM-1 and VCAM-1 by TNFα (FIG. 3). When RAOECs were treated with OXNB, adhesion of NR8383 to RAOECs was significantly decreased (FIG. 4). Similar results were obtained in the experiments using IL-1β instead of TNFα. As shown in FIG. 5, OXNB did not inhibit activation of c-Jun NH2 terminal kinase (JNK). OXNB did not affect degradation of IKBα that is an internal inhibitor for NFkB (FIG. 6A). Consequently, activation of NFkB was not decreased by treatment of OXNB (FIG. 6B). These results suggest that intracellular signal transduction was not changed by OXNB. These results indicate that OXNB might affect transcriptional regulation of VCAM-1 by TNFα. Curcumin, a specific HAT inhibitor is reported to inhibit TNFα-induced VCAM-1 expression (Lee C W, Lin W N, Lin C C, Luo S F, Wang J S, Pouyssegur J, Yang C M: Transcriptional regulation of VCAM-1 expression by tumor necrosis factor-a in human tracheal smooth muscle cells: Involvement of MAPKs, NF-kB, p300 and histone acetylation. J Cell Physiol. 2006; 207: 174-186). Thus it is possible that OXNB attenuates VCAM-1 expression via an inhibition of HAT in endothelial cells. We investigated the effect of OXNB on HAT activity in RAOECs. We observed that OXNB inhibited the acetylation of histone H3 (FIG. 7). Acetylation of histone H4 was not changed by OXNB. Similar results were obtained when ozone nanobubbles are used instead of OXNB.

Conclusion:
These results indicate that nano-bubbles (OXNB and OZNB) could be a novel therapeutic measure to attenuate atherosclerosis via a selective inhibition of histone H3 acetylation of in vitro cultured endothelial cells.

Example 2

Objective:
To investigate the effect of nano-bubbles on hypertrophic response of vascular smooth muscle cells.

Methods:
(1) Medium preparation: DMEM media for vascular smooth muscle cells were prepared with the same procedure of MCDB media in Example 1.

(2) Cell culture: Rat aortic vascular smooth muscle cells (RASMCs, passage 7 to 10) were used. RASMCs were incubated in the serum free DMEM media with or without OXNB (75%) for 48 hours and were stimulated with A II (A II, $10^{-8}$ M), epidermal growth factor (EGF, 100 ng/mL) or platelet-derived growth factor (PDGF, 50 ng/mL).

(3) Signal transduction analysis: Activation of extracellular signal-regulated kinase (ERK) was evaluated by Western blotting analysis. Tyrosine phosphorylation of EGF receptor was analyzed by immunoprecipitation (IP) of EGF receptor with immunoblotting with anti-phosphotyrosine (clone 4G10).

(4) Protein content and the viable cell number: Protein content of cell lysate from RASMCs was measured by chromomeric assay using bicinchoninic acid solution. Cell viability was measured by dehydrogenase enzyme activity found in metabolically active cells using 3-(4,5-dimethylthiazol-2-yl)-5-(3-carboxymethoxyphenyl)-2-(4-sulfophenyl)-2H-tetrazolium, inner salt; MTS.

Figure 8:
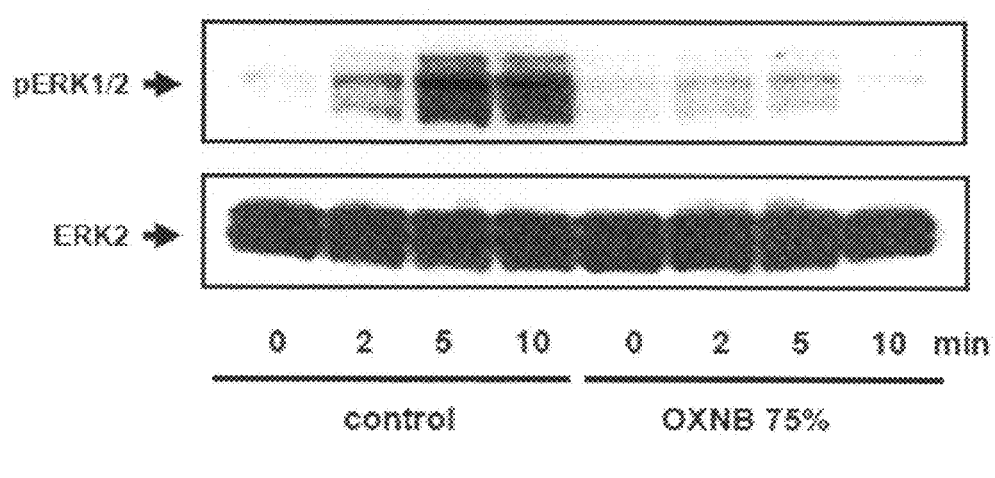
FIG. 8 shows results of signal transduction experiments in Example 2.
Figure 9A:
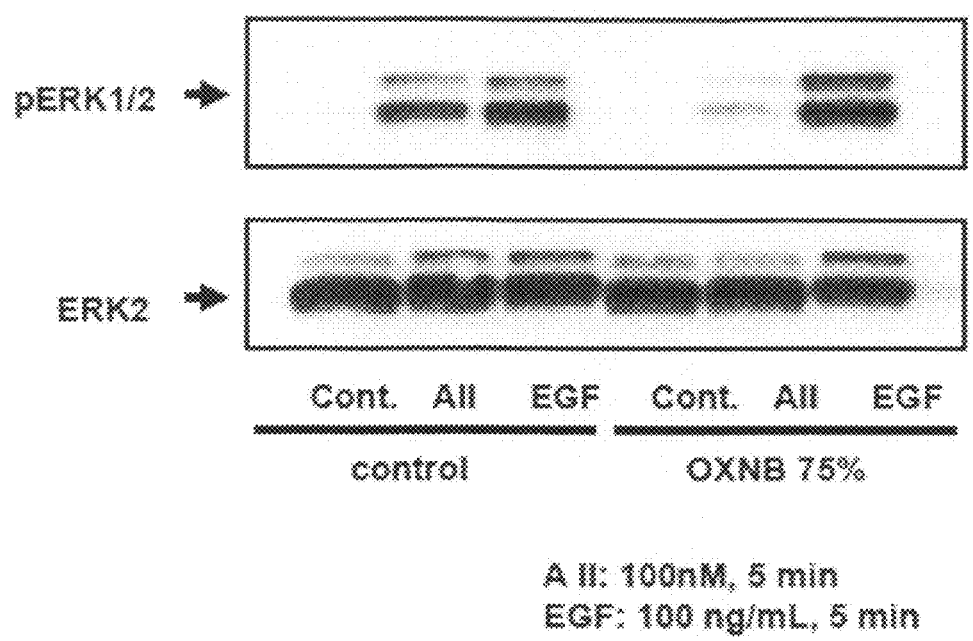
FIG. 9A shows results of signal transduction experiments in Example 2.
Figure 9B:
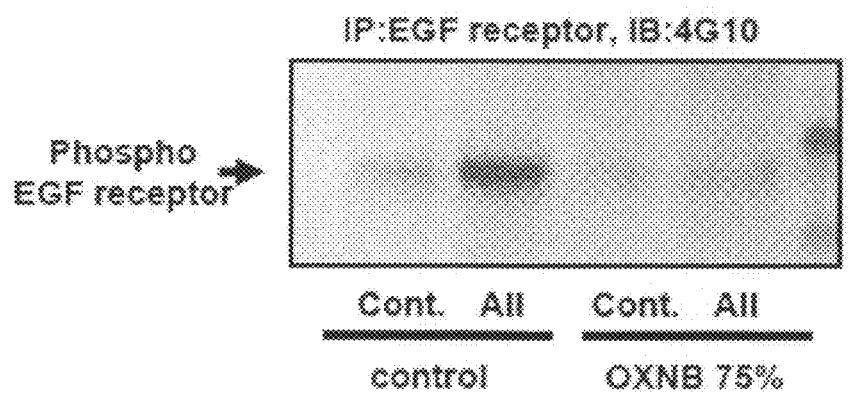
FIG. 9B shows results of signal transduction experiments in Example 2.
Figure 10A:
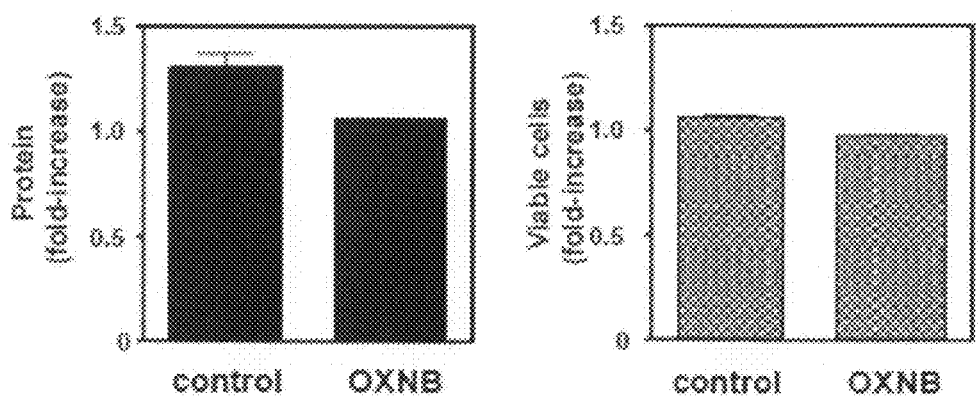
FIG. 10A is a graph showing the results of the evaluation of protein content and viable cell number in Example 2.
Figure 10B:
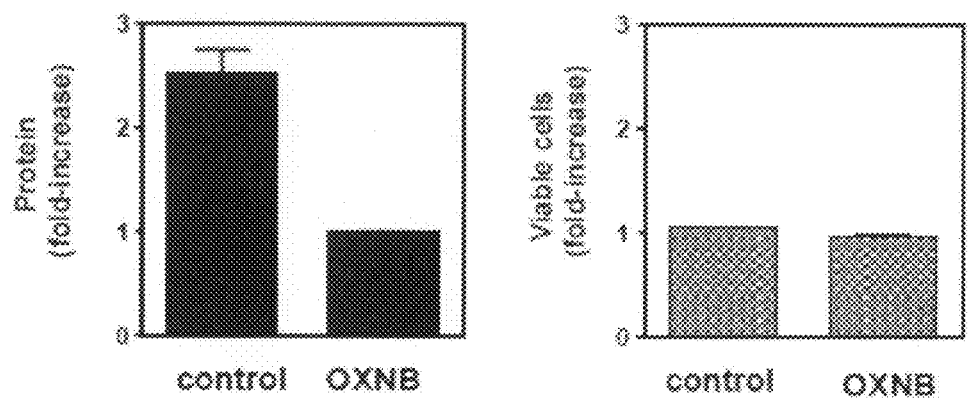
FIG. 10B is a graph showing the results of the evaluation of protein content and viable cell number in Example 2.

Results:

FIG. 8 shows the time course of ERK activation by A II. DMEM containing 100%-OXNB inhibited ERK activation by A II over 10 minutes. As shown in FIG. 9A, A II and EGF activated ERK in RASMCs 5 minutes after the stimulation. Treatment of RASMCs with OXNB inhibited ERK activation by A II, however ERK activation by EGF was not changed suggesting the specific inhibition of A II-mediated ERK activation. It has been reported that transactivation of EGF receptor has an important role in ERK activation by A II (H Daub, C Wallasch, A Lankenau, A Herrlich, A Ullrich: Signal characteristics of G protein-transactivated EGF receptor. EMBO J. 1997; 16: 7032-7044). We checked the effect of OXNB on transactivation of EGF receptor by A II. As shown in FIG. 9B, OXNB inhibited transactivation of EGF receptor, suggesting that decreased ERK activation is at least, partially mediated by an inhibition of EGF receptor transactivation. As we found the inhibitory effect of OXNB on ERK activation, we have investigated the effect of OXNB on protein synthesis of RASMCs. As shown in FIG. 10A, A II increased protein content of RASMCs under inhibition of A II type-2 receptor ($10^{-6}$ M of PD123319). No significant change was observed in cell viability by A II, suggesting that A II promotes hypertrophy of RASMCs. OXNB inhibited this hypertrophic response of RASMCs by A II. Similarly PDGF increased protein content of RASMCs without changing the viable cell number. OXNB significantly inhibited the increases in protein content in RASMCs without affecting the viable cell number (FIG. 10B). Similar results were obtained in the experiments using OZNB instead of OXNB.

Conclusion:

These results suggest that nano-bubbles inhibit hypertrophy of vascular smooth muscle cells. It is possible that nano-bubbles attenuate vascular remodeling induced by atherogenic stimuli.

Example 3

Objective:

To investigate the in vivo effect of OXNB using the animal model of genetic hypertension.

Methods:

Spontaneously hypertensive rats (SHR) at 4 week-old were used. SHR were divided into control (n=4) and OXNB group (n=4). They were kept in the separated cages and allowed to drink either water with 0.1% by mass of NaCl or water with 10-fold diluted OXNB with 1% by mass of NaCl (final concentration of 0.1% by mass of NaCl). The amount of water intake, body weight, systolic blood pressure (SBP) and pulse rate (PR) were checked once a week. They were sacrificed at 40 week-old to examine histological changes in hypertension-target organs (heart and kidney).

Figure 11:
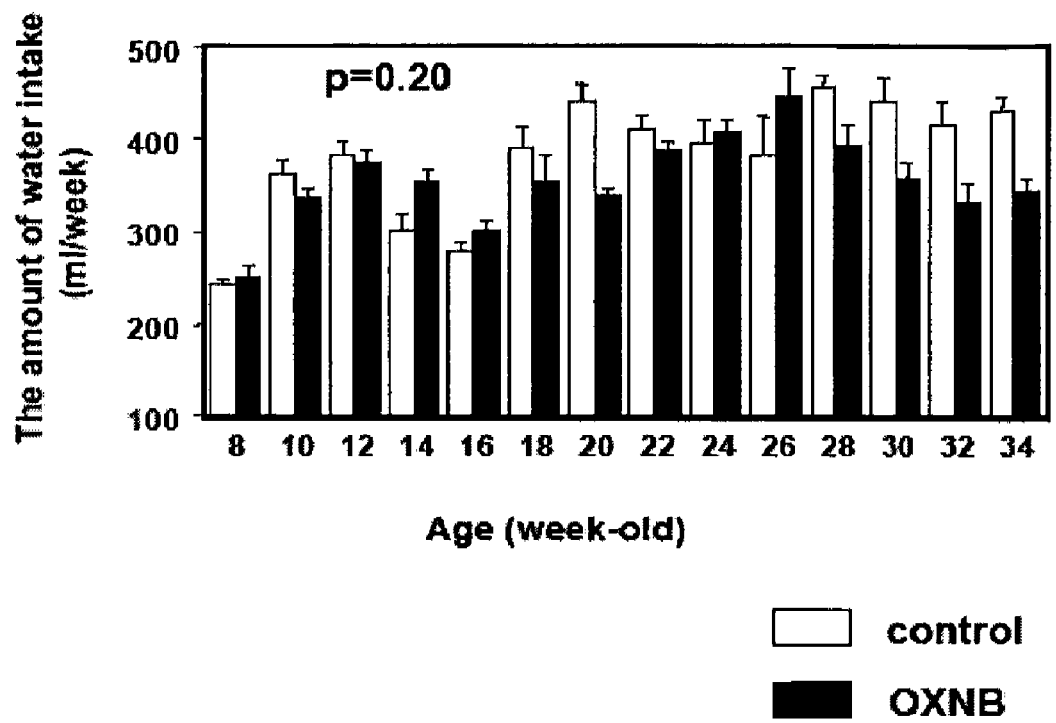
FIG. 11 is a graph showing the results of the evaluation of amount of water intake in Example 3.
Figure 12:
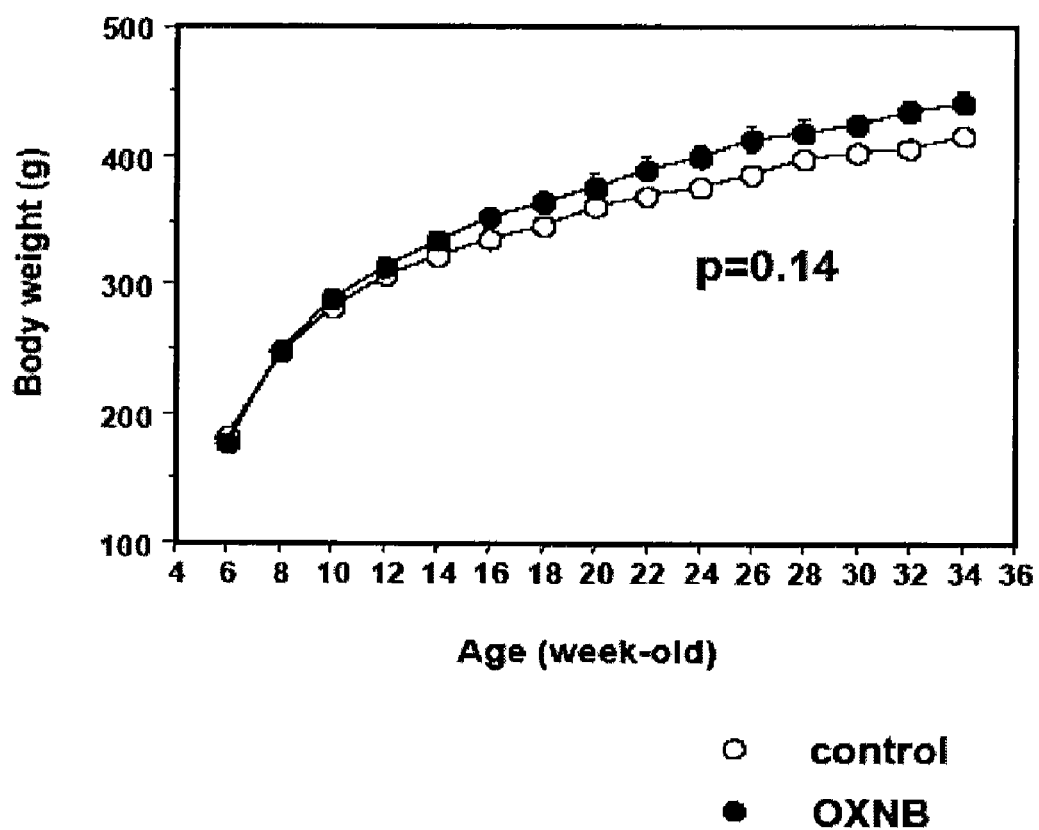
FIG. 12 is a graph showing the results of the evaluation of body weight in Example 3.
Figure 13:
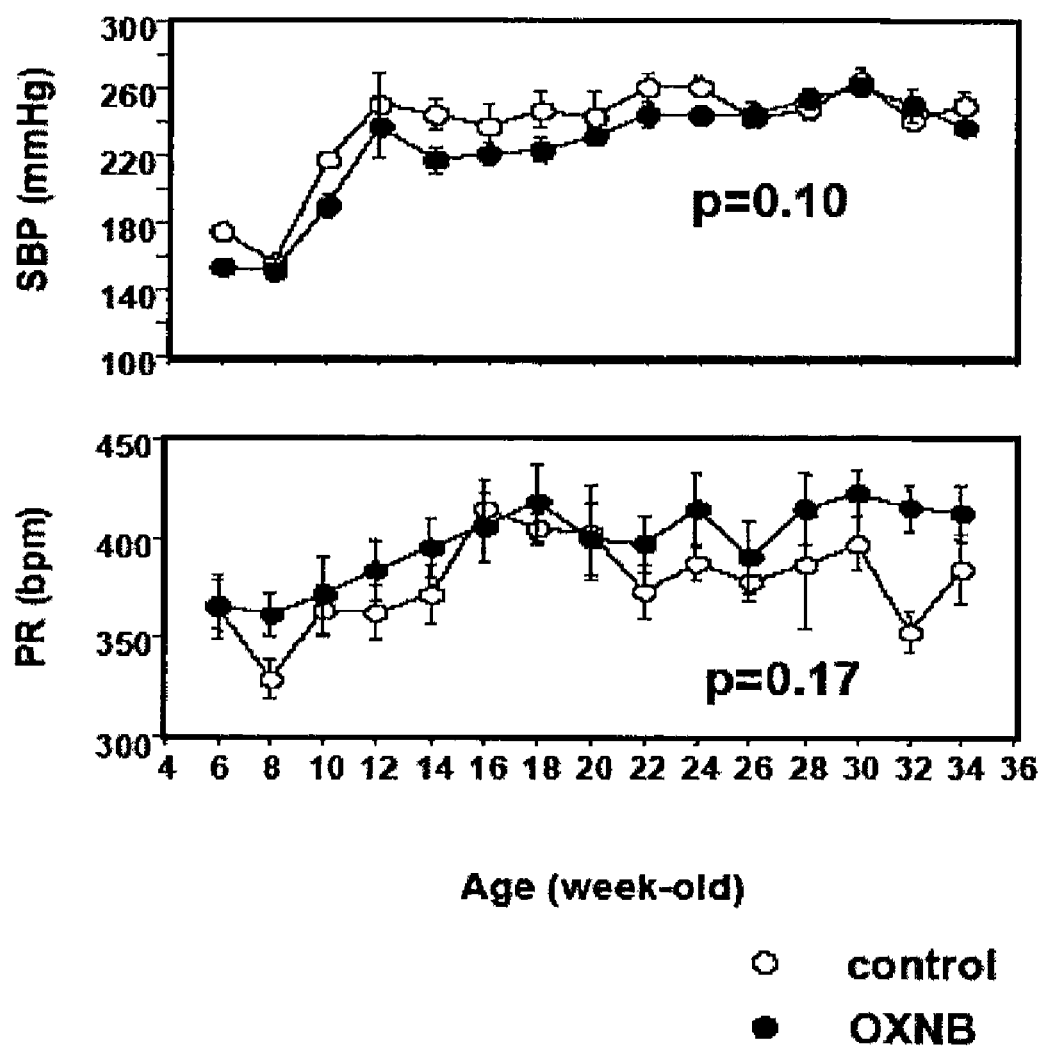
FIG. 13 is a graph showing the results of the evaluation of systolic blood pressure and the evaluation of pulse rate in Example 3.

Results:

As shown in FIG. 11, the amount of water did not differ between two groups. Body weight in OXNB group was higher than that in control group (FIG. 12). Blood pressure and pulse rate were not significantly different between two groups (FIG. 13). The organ weight ratio of heart and kidney did not differ between two groups (Table 1). As shown in FIG. 14, hematoxylin-eosin staining of glomerular apparatus in SHR kidney showed marked hyaline degeneration. In contrast, OXNB group did not show any degenerative changes in the kidney. The quantitative analysis of histological specimen revealed that the administration of OXNB to SHR decreased the degeneration rate of glomerular apparatus significantly (control: 92.1+/−0.49%, OXNB: 24.4+/−5.8%, p<0.001).

We also did the same experiments using OZNB and found protective effect of OZNB in SHR kidney. No significant histological changes were found in the heart.

TABLE 1

| The organ to body weight ratio in SHR | | | |
|---|---|---|---|
| | Control | OXNB | p value |
| Heart (g/kg) | 4.88 ± 0.38 | 4.72 ± 0.42 | 0.79 |
| Right kidney (g/kg) | 5.03 ± 0.36 | 5.50 ± 0.53 | 0.53 |

We checked the effect of OXNB on the redox state in SHR because the excess administration of oxygen might results in the increase in oxidative stress. We have measured the plasma levels of low density lipoprotein cholesterol (LDL-cholesterol), a marker of oxidative stress, in SHR. We did not find significant changes in plasma LDL cholesterol levels in the two groups (control: 59.8+/−9.6 mg/dL, OXNB: 71.0+/−2.1 mg/dL, p=0.30).

Conclusion:

These results suggest that OXNB prevented glomerular injury in the hypertension model animals. This protective effect of glomerular apparatus is exerted without reducing blood pressure, suggesting that nano-bubbles can protect kidneys even the blood pressure is elevated. The anti-inflammatory and anti-proliferative property of nano-bubbles is supposed to be involved in this unique biological activity such HAT inhibition.

(Conclusions)

OXNB and OZNB prevented glomerular injury in the animal models of hypertension. The renal protective effect might be exerted by attenuation of inflammation and remodeling of blood vessels. Inhibition of HAT is at least, partially involved in the mechanism. Precise mechanism how nano-bubbles inhibit HAT is still not clear, however this property of nano-bubbles might be applied to other diseases such as atherosclerosis, heart failure and cerebrovascular diseases. Application of nano-bubbles could be a novel treatment for renal diseases caused by hypertension. This technology might be applied in immunological, diabetic and drug-induced glomerular injury that shares common pathogenic features with hypertensive renal disease.

What is claimed is:

1. A method of treating a disease exacerbated by vascular smooth muscle cell hypertrophy in a patient in need thereof, comprising contacting at least one composition selected from the group consisting of oxygen nanobubble water and ozone nanobubble water with endothelial cells, so that vascular smooth muscle cell hypertrophy is inhibited in the endothelial cells.

2. A method for inhibiting hypertensive glomerular injury, comprising administering at least one composition selected from the group consisting of oxygen nanobubble water and ozone nanobubble water to an animal hypertension.

3. A method for treating a disease resulting from remodeling in a blood vessel, comprising
administering a medical agent comprising at least one composition selected from the group consisting of oxygen nanobubble water and ozone nanobubble water to a patient having a disease resulting from remodeling in a blood vessel, so that the medical agent contacts with a tissue in a blood vessel where remodeling has occurred.

4. The method according to claim 3, wherein the disease is at least one selected from arteriosclerosis, heart failure, cerebrovascular disorder, and hypertensive kidney disease.

* * * * *